US006245757B1

(12) United States Patent
Chopp et al.

(10) Patent No.: US 6,245,757 B1
(45) Date of Patent: Jun. 12, 2001

(54) USE OF PROGESTINS TO TREAT ISCHEMIC EVENT

(75) Inventors: Michael Chopp, Southfield, MI (US); Ning Jiang, Pittsburg, PA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/164,485

(22) Filed: Oct. 1, 1998

Related U.S. Application Data

(60) Provisional application No. 60/060,804, filed on Oct. 3, 1997.

(51) Int. Cl.$^7$ ..................................................... A61K 31/56

(52) U.S. Cl. ............................................ 514/177; 514/177

(58) Field of Search .............................................. 514/177

(56) References Cited

U.S. PATENT DOCUMENTS 5,380,839    1/1995  McCall et al. ....................... 540/111

OTHER PUBLICATIONS

*Remington's Pharmaceutical Sciences, 18th Edition,* Gennaro, A.R., (ed.), Mack Publishing Company, Easton, PA, p. 990–993 (1990).
Bäckström, T., et al., "Effects of Intravenous Progesterone Infusions on the Epileptic Discharge Frequency in Women with Partial Epilepsy", *Acta Neurol. Scand.,* 69, 240–248, (1984).
Betz, A.L., et al., "Effect of Steroids on Edema and Sodium Uptake of the Brain During Focal Ischemia in Rats", *Stroke,* 21, 1199–1204 (1990).
Block, G.A., et al., "The Adenosine Agonist, R–Phenylisopropyladenosine, Attenuates Ischemic Neuronal Damage", *Journal of Cerebral Blood Flow and Metabolism,* 7, Abstract No. XII–6, p. S258 (1987).
Bouma, G.J., et al., "Cerebral Circulation and Metabolism after Severe Traumatic Brain Injury: the Elusive Role of Ischemia", *J. Neurosurg.,* 75, 685–693 (1991).
Chumas, P.D., et al., "A Comparison of the Protective Effect of Dexamethasone to Other Potential Prophylactic Agents in a Neonatal Rat Model of Cerebral Hypoxia–Ischemia", *J. Neurosurg.,* 79, 414–420 (1993).
De Reuck, J., et al., "Steroid Treatment in Acute Ischaemic Stroke", *Eur. Neurol.,* 28, 70–72 (1988).
DeLeo, J., et al., "Propentofylline (HWA 285) Protects Hippocampal Neurons of Mongolian Gerbils against Ischemic Damage in the Presence of an Adenosine Antagonist", *Neuroscience Letters,* 84, 307–311 (1988).
DeWitt, D.S., et al., "Reduced Cerebral Blood Flow, Oxygen Delivery, and Electroencephalographic Activity after Traumatic Brain Injury and Mild Hemorrhage in Cats", *J. Neurosurg.,* 76, 812–821 (1992).

Ekert, P., et al., "Dexamethasone Prevents Apoptosis in a Neonatal Rat Model of Hypoxic–Ischemic Encephalopathy (HIE) by a Reactive Oxygen Species–Independent Mechanism", *Brain Research,* 747, 9–17 (1997).
Graham, D.I., et al., "Ischaemic Brain Damage in Fatal Non–Missile Head Injuries", *Journal of the Neurological Sciences,* 39, 213–234 (1978).
Graham, D.I., et al., "Ischaemic Brain Damage is Still Common in Fatal Non–Missile Head Injury", *Journal of Neurology, Neurosurgery, and Psychiatry,* 52, 346–350 (1989).
Hoffman, S.W., et al., "A Reliable and Sensitive Enzyme Immunoassay Method for Measuring 8–isoprosaglandin $F_{2\alpha}$: a Marker for Lipid Peroxidation after Experimental Brain Injury", *Journal of Neuroscience Methods,* 68, 133–136 (1996).
Jarrott, D.M., et al., "A Gerbil Model of Cerebral Ischemia Suitable for Drug Evaluation", *Stroke,* 11, 203–209 (Mar.–Apr. 1980).
Jenkins, L.W., et al., "Increased Vulnerability of the Traumatized Brain to Early Ischemia", Source Unavailable, p. 273–282 (Date Unavailable).
Kelly, D.F., "Steriods in Head Injury", *New Horizons,* 3, 453–455 (1995).
Kogure, K., et al., "An Effect of Aminophylline in Experimental Cerebral Ischemia", *Trans. Am. Neurol. Assoc.,* 100, 77–80 (1975).
Koide, T., et al., "Chronic Dexamethasone Pretreatment Aggravates Ischemic Neuronal Necrosis", *Journal of Cerebral Blood Flow and Metabolism,* 6, 395–404 (1986).
Lekieffre, D., et al., "Increased Neurosteroid Synthesis in the Rat Brain Induced by Global Ischemia", *Society for Neuroscience,* 21, Abstract No. 94.14, p. 230 (1995).
McGraw, C.P., et al., "Effect of Aminophylline on Cerebral Infarction in the Mongolian Gerbil", *Stroke,* 9, 477–479 (1978).
Morali, G., et al., "Effects of Progesterone Upon the Brain Damage Induced by Acute Global Cerebral Ischemia in Cats", *Journal of Neuropathology and Experimental Neurology,* 56, Abstract No. 113, p. 599 (May 1997).
Roof, R.L., et al., "Gender Influences Outcome of Brain Injury: Progesterone Plays a Protective Role", *Brain Research,* 607, 333–336 (1993).
Roof, R.L., et al., "Progesetrone Facilitates Cognitive Recovery and Reduces Secondary Neuronal Loss Caused by Cortical Contusion Injury in Male Rats", *Experimental Neurology,* 129, 64–69 (1994).

(List continued on next page.)

Primary Examiner—Zohreh Fay
(74) Attorney, Agent, or Firm—Schwegman, Lundberg, Woessner & Kluth, P.A.

(57) ABSTRACT

A method for the treatment of ischemic damage, such as damage due to stroke or myocardial infarction, is provided, comprising administering to a mammal afflicted with stroke, an effective amount of a progestin in a suitable vehicle.

20 Claims, 5 Drawing Sheets

OTHER PUBLICATIONS

Roof, R.L., et al., "Progesterone Treatment Attenuates Brain Edema Following Contusion Injury in Male and Female Rats", *Restorative Neurology and Neuroscience,* 4, 425–427 (1992).

Roussel, S., et al., "Focal Cerebral Ischemia in Chronic Hypertension: No Protection by (R)—phenylisopropyladenosine", *Brain Research,* 545, 171–174 (1991).

Rudolphi, K.A., et al., "Effect of Theophylline on Ischemically Induced Hippocampal Damage in Mongolian Gerbils: A Behavioral and Histopathological Study", *Journal of Cerebral Blood Flow and Metabolism,* 7, 74–81 (1987).

Seida, M., et al., "Effect of Aminophylline on Postischemic Edema and Brain Damage in Cats", *Stroke,* 19, 1275–1282 (1988).

Smith–Swintosky, V.L., et al., "Metyrapone, an Inhibitor of Glucocorticoid Production, Reduces Brain Injury Induced by Focal and Global Ischemia and Seizures", *Journal of Cerebral Blood Flow and Metabolism,* 16, 585–598 (1996).

Tuor, U.I., et al., "Prevention of Neonatal Hypotoxic–Ischemia Brain Damage with Dexamethasone: Age Dependence of Response", *Pharmacology of Ischemia,* Abstract No. P13.20.8, p. 434 (1994).

Wass, C.T., et al., "Insulin Treatment of Corticosteroid–Associated Hyperglycemia and Its Effect on Outcome after Forebrain Ischemia in Rats", *Anesthesiology,* 84, 644–651 (1996).

Medline Abstract 97061144. Chopp et al, Sep. 1996.*

* cited by examiner

USE OF PROGESTINS TO TREAT ISCHEMIC EVENT

This application claim benefit to provisional application 60/060,804 filed Oct. 3, 1997.

BACKGROUND OF THE INVENTION

Oxygen is supplied to the cells by the blood and most cellular energy production is tightly coupled to oxygen. Whenever the blood flow to an organ is interrupted, a state of ischemia exists. During ischemia, cellular ATP will be consumed and usually cannot adequately be replenished in the absence of a supply of oxygen. Ischemia can exist for only a portion of an organ when the blockage of the blood supply to the organ is not total. In addition to total ischemia, or no blood flow, there are intermediate degrees of ischemia.

Significant ischemia occurs in stroke and during most cases of open heart surgery, all episodes of coronary occlusion or heart attack, all cases of organ transplantation, certain procedures such as liver shunt operations and a variety of other situations in which either significant stress or a period of shock has compromised the functioning of one or more organs of the body. In all of these situations, cellular energy metabolism is impaired, and its restoration is critical to the recovery of organ function.

For example, stroke, or cerebrovascular disease, is the name for several disorders that occur within seconds or minutes after the blood supply to the brain is disturbed. Stroke is the third leading cause of death in developed countries. Approximately 550,000 Americans suffer a stroke each year; one fourth of them die and half of the survivors have residual disabilities, including paralysis of face or extremities, speech disorders, loss of bladder function, inability to swallow or dementia. Stroke is the principal cause of severe disability, often requiring institutionalization of stroke survivors at a total cost in the U.S. of $20 to 30 billion dollars per year. Stroke is more likely to occur in the elderly, and the risk doubles each decade after age 35 years. Five percent of the population older than 65 years has had a stroke.

Symptoms of stroke may progress or fluctuate during the first day or two after onset; this is called evolution. When no further deterioration occurs, the condition is considered to be a completed stroke. The only warning signal that suggests susceptibility to a stroke is a transient ischemic attack (TIA).

Strokes are characterized by the location and type of disturbance. The most common is a deficient supply of blood through an artery (ischemia). About 84% of strokes (about 400,000 per year in the U.S.) result from occlusion of cerebral arteries by blood clots. Ischemic cell damage follows rapidly upon interruption of the blood supply downstream from the clot. The remaining 16% of strokes are the result of intracerebral or subarachnoid hemorrhage. While hemorrhage induces other injurious events, ischemia resulting from the "short circuited" blood flow is still a significant factor in neuronal damage from hemorrhagic strokes.

Cell death occurs rapidly in the core region of a stroke, where blood flow is reduced to about 20% of normal. However, there is a larger area of potential injury, called the ischemic penumbra, where blood flow is reduced to a lesser extent. Cells in this region are endangered, but may not be irreversibly damaged. It is this penumbral area wherein neuroprotective agents may have their most beneficial effects in preventing cell damage and death due to ischemia and thereby reducing the incidence of long term disabilities.

Pharmacological intervention into the stroke process has not been successful. For example, studies evaluating the effectiveness of corticosteroids in the setting of head injury or global or focal brain ischemia have demonstrated either no improvement or a worsening of neurological outcome. See, for example, C. T. Wass et al., *Anesthesiology*, 84, 644 (1996) and references cited therein. A study of stroke patients treated primarily with dexamethasone or methylprednisolone showed no significant difference in outcome between steroid and non-steroid treated patients. J. DeReuck et al., *Eur. Neurol.*, 28, 70 (1988).

Due to the lack of available pharmacotherapeutic agents, a significant percentage of the population subject to stroke or its after effects are poorly managed. None of the drugs presently available are capable of preventing damage due to stroke and most, such as anticoagulants, which can be shown to speed clot dissolution and hasten reperfusion if given within three hours of the onset of ischemia, have disturbing side effects. Anticoagulants can in fact be fatal if used inappropriately, e.g., for treating a hemorrhagic stroke. Clearly, current therapy has failed to "seize control" of this debilitating pathology.

Therefore, an object of this invention is to provide pharmaceutical agents useful in the treatment of stroke.

A further object of this invention is to provide a method of treating stroke and related ischemic disorders.

SUMMARY OF THE INVENTION

The present invention provides a method to treat cell damage due to ischemia, as caused by stroke or infarct comprising administering to a mammal afflicted with ischemic cell damage, an effective amount of a pharmaceutical composition comprising a progestin in combination with a pharmaceutically acceptable liquid delivery vehicle, following onset of ischemia. The amount of progestin is effective to ameliorate or mitigate at least one of the effects of ischemia, such as the acute phase of stroke, myocardial or pulmonary infarction or their aftereffects, such as those described hereinabove. It is believed that the present method functions, at least in part, by the ability of the progestin to reduce the damage caused by ischemia, i.e., the brain damage caused by cerebral ischemia, and its aftereffects. The efficacy of the present method may also be due to enhancement of the ability of the brain to recognize after damage, by enhancing its intrinsic ability to compensate for injury.

As used herein the term "progestin" or "progestogen" includes the steroid hormones disclosed under that designation in *Remington's Pharmaceutical Sciences*, A. R. Gennaro, ed., Mack Publishing Co. (18th ed. 1990) at pages 990–993, as well as their derivatives and bioactive metabolites. A preferred progestin for use in the present method is progesterone (pregn-4-ene-3,20-dione), its metabolites such as 5-dehydroprogesterone and allopregnanolone, and related compounds such as 5-pregnane-3,20-dione.

In order for a product to have utility in treating cell damage due to ischemia from conditions such as stroke, the product must provide a "clinical improvement" to the host when administered after the ischemic event has occurred. Functional outcome is the primary endpoint used by the FDA to evaluate therapeutic interventions for stroke. For the stroke patient a number of scales, including the Barthel index and the NIH stroke scale are employed as primary outcome measures. The critical endpoint for any effective therapy for stroke is improvement of neurologic function. Therefore, a successful therapeutic intervention in an experimental stroke model must reduce neurologic deficits. The present invention demonstrates for the first time that a progestin can be administered to a mammal after the onset of an ischemic event and significantly improve clinically relevant end points or physiological conditions such as neurological function and weight loss, compared to mammals not receiving the treatment.

Progesterone has been used in previous studies involving models of ischemia; however the progesterone was delivered prior to the onset of the occlusion and no improvement was seen in clinically relevant physiological conditions. Progesterone administered to rats one hour prior to middle cerebral artery occlusion was reported by A. L. Betz et al., *Stroke*, 21, 1199 (1990) to reduce brain edema in the early stages of ischemia. In the Betz work, focal ischemia was induced following extensive surgical intervention, including craniotomy to expose the brain. Such extensive surgical manipulation alone is sufficient to induce severe edema, apart from any edema attributable to the ischemia. This fact was noted in the report, where it was stated that control animals did not have a craniotomy because such a procedure itself would induce edema. Therefore, it is not clear how much the edema in those animals was the result of the focal ischemia or the procedure used to achieve the ischemia. The Betz work also does not suggest that progesterone would be effective after the onset of ischemia, although one might expect the surgically induced edema to be mitigated in those animals. In other studies, G. Morali et al., *J. Neuropath. & Exp. Neurol.*, 56, A113 (1997) showed that progesterone exhibited neuroprotective activity following global cerebral ischemia only after a 7-day pretreatment regimen. However, global cerebral ischemica is a different pathology than stroke, causing selective neuronal damage, as opposed to the widespread cellular neurosis caused by stroke. Thus, the prior art does not suggest that progesterone, when given only after an ischemic event, would be effective in mitigating the direct effects of ischemia, despite any effects it might have on edema.

On the other hand, the relationship of edema resulting from physical trauma or surgical manipulation, to ischemic cell damage following a stroke is not at all clear. Ischemia in the penumbral region of a stroke infarct results from an interruption of blood flow due generally to a clot. Edema, to the degree to which it occurs, is a secondary phenomenon. While edema may secondarily induce additional ischemia, the degree to which it may be a critical clinical factor in management of stroke is not clear. In any event, prevention or reduction of edema by progesterone, as in the Betz paper, or by glucocorticoids (J. DeReuck et al.,*Eur. Neurol.*, 28, 70 (1988)) does not appear to correlate with improved clinical outcome in stroke patients or in animal models of stroke.

Roof and coworkers (R. L. Roof et al., *Restor. Neurol. Neurosci.*, 4, 425, (1992), R. L. Roof et al., *Exp. Neurol.*, 129, 64 (1994)) showed that progesterone treatment reduced edema resulting from cerebral contusion when the drug was given one hour after the cerebral trauma. Roof also showed (*Brain Res.*, 607, 333 (1993)) that decreased cerebral edema subsequent to brain contusion is associated with high levels of circulating progesterone and is independent of estrogen levels. However, the Roof work involved direct cerebral trauma, a blow sufficient to depress the cortical structure of the test animals. In these instances, edema was the primary cause of cell injury, not ischemia, and agents that reduce edema would be expected to mitigate the injury it causes.

We have discovered that progesterone, when administered in a clinically acceptable vehicle that facilitates rapid transport of the steroid to the brain, is effective in reducing infarct size following acute, focal ischemia, not only when given prior to the onset of ischemia, but also, surprisingly, when given 2–3 hours after ischemia onset. Not only was infarct size reduced, but neurological defects were reduced in the treated animals. The examples disclosed hereinbelow demonstrate that progesterone treatments were as effective whether when given 2 hours after the onset of middle cerebral artery occlusion (MCAO), as they were when given prior to onset of MCAO, in a model of focal ischemia wherein the contribution of secondary edema resulting from surgical trauma was minimized. Thus, effective amounts of progesterone and other progestins can be delivered, as by injection or infusion, after the acute phase of stroke, in order to mitigate or block the effects of stroke-induced ischemia.

Although the studies of the Examples are directed at enhancing the energetic recovery following ischemia of the brain, the present method is expected to be applicable to any tissue or organ that has suffered an ischemic insult. These situations include but are not limited to: myocardial infarction, stroke, organ transplant with organ preservation, neonatal support, multi-organ system failures, shock and trauma resulting in compromised circulation, and the like. Often, even uncomplicated general anesthesia can result in some degree of hypoxia. Therefore, the present invention provides a method whereby ischemic tissue, including tissue of the central nervous system or muscle tissue, can be treated so as to improve tissue survival and to hasten general bodily recovery.

DETAILED DESCRIPTION OF THE INVENTION

Figure 1:
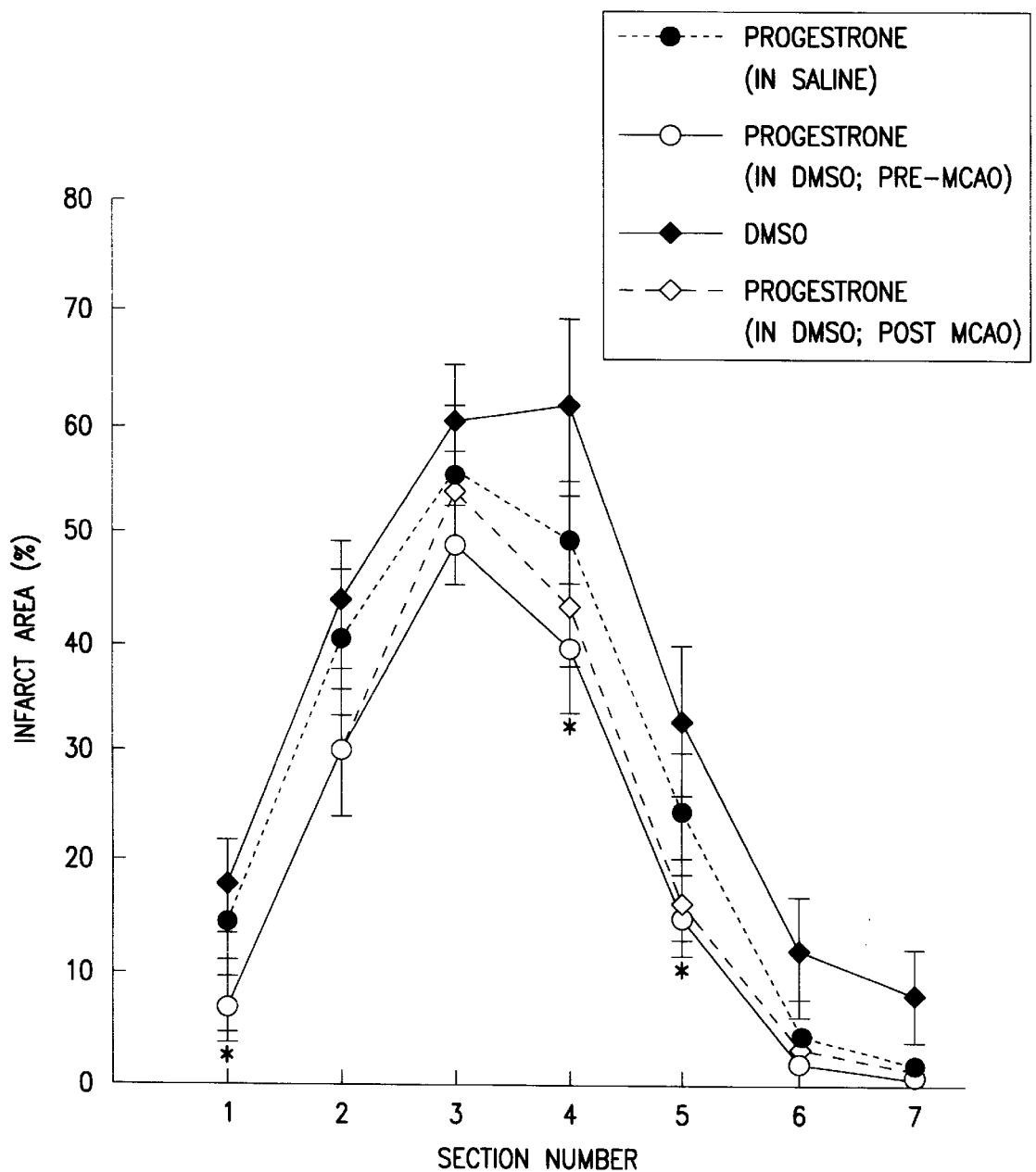
FIG. 1 is a graph showing the percent area of infarction to the area of the contralateral hemisphere in each of seven forebrain sections in PROGs and DMSO treated groups. Values are mean ±S.E.M. P<0.05 versus DMSO group.

Progestins useful in the present method include progesterone, 5-dehydroprogesterone, 6-dehydroretroprogesterone(dydrogesterone), allopregnanolone (allopregnan-3α, or 3β-ol-20-one), ethynodiol diacetate, hydroxyprogesterone caproate (pregn-4-ene-3,20-dione, 17-(1-oxohexy)oxy); levonorgestrel, norethindrone, norethindrone acetate (19-norpregn-4-en-20-yn-3-one, 17-(acetyloxy)-,(17α)-); norethynodrel, norgestrel, pregnenolone, and megestrol acetate. Useful progestins also can include allopregnone-3α or 3β, 20α or 20β-diol (see Merck Index, 12th ed., 266–286); allopregnane-3β, 21-diol-11,20-dione; allopregnane-3β, 17α-diol-20-one; 3,20-allopregnanedione, allopregnane,3β, 11β, 17α,20β,21-pentol; allopregnane-3β, 17α,20β, 21-tetrol; allopregnane-3α or 3β, 11β, 17α,21-tetrol-20-one, allopregnane-3β, 17α, 20α or 20β-triol; allopregnane-3β, 17α, 21-triol-11,20-dione; allopregnane-3β, 11β,21-triol-20-one; allopregnane-3β, 17α, 21-triol-20-one; allopregnane-3α or 3β-ol-20-one;

pregnanediol; 3,20-pregnanedione; pregnan-3α-ol-20-one; 4-pregnene-20,21-diol-3,11-dione; 4-pregnene-11 β, 17α, 20β,21-tetrol-3-one; 4-pregnene-17α,20β,21-triol-3,11-dione; 4-pregnene-17α,20β,21-triol-3-one, and pregnenolone methyl ether, as well as derivatives thereof such as esters with non-toxic organic acids such as acetic acid, benzoic acid, maleic acid, malic acid, caproic acid, citric acid and the like. water-soluble or solulizable progestins such as progesterone, are preferred for use in the present method.

Apart from their use in fertility control, progestins, particularly progesterone (PROG), exert various actions in the central nervous system (CNS). PROG receptors are widely distributed in the CNS, including hypothalamus, preoptic area, midbrain, cortex, amygdala, hippocampus, caudateputamen and cerebellum (N. J. MacLusky et al., *Nature*, 274, 276 (1978)). Moreover, in addition to its synthesis in endocrine organs (ovary, corpus luteum and adrenal gland), PROG is synthesized locally within central and peripheral nervous tissues (P. Robel et al., *Neurochem. Int.*, 7, 953 (1985); P. Robel et al., *J. Steroid Biochem.*, 27, 649 (1987); H. L. Koenig et al., *Science*, 268 ,1500 (1995)).

The presence of receptors and sources of PROG within the nervous system as well as its modulation of inhibitory and excitatory amino acids suggest a broader role for PROG than simply as a gestational hormone. PROG and its related metabolites are CNS depressants and exert anesthetic, anticonvulsant and anxiolytic actions by modifying the function of GABA and EAA neurotransmitter systems in the CNS. See, for example, M. Bixo et al., *Psychoneuroendo.*, 15, 159 (1990); S. O. E. Landgren et al., *Epilepsy Res.*, 10, 156 (1991); M. D. Majewska et al., *Science*, 232, 1004 (1986) and B. C. Litter et al., *J. Nerv. Ment. Dis.*, 159, 256 (1974). However, the relationship of these CNS activities of progesterone to any beneficial effects of the steroid on ischemic damage is not understood.

In cases where progestins are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The progestins can be formulated as pharmaceutical compositions and administered to a mammalian host, such as a human patient in a variety of unit dosage or sustained release forms adapted to the chosen route of administration, i.e., orally or parenterally, by intravenous, intrathecal, intramuscular, topical or subcutaneous routes.

Thus, the progestins may be systemically administered, e.g., orally, in combination with a pharmaceutically acceptable vehicle or carrier such as an inert diluent or an assimilable edible carrier. They may be enclosed in hard or soft shell gelatin capsules, may be compressed into tablets, encapsulated in liposomes, and/or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices, such as patches or implantable depots or pumps.

The active compound may also be administered intravenously, intrathecally, intraperitoneally, or by infusion or injection. Solutions of the active compound or its salts can be prepared in water DMSO or mixtures thereof, optionally mixed with a nontoxic surfactant or alcohol. Other lipophilic vehicles can be employed, such as fixed oils, and cyclodextrins can be used to solubilize the progestin in water, if necessary. Under ordinary conditions of storage and use, these preparations can contain a preservative to prevent the growth of microorganisms.

The pharmaceutical dosage forms suitable for injection, inhalation, insufflation or infusion can include sterile solutions or dispersions or sterile powders comprising one or more progestins which are adapted for the contemporaneous preparation of sterile injectable or infusible solutions or dispersions, optionally encapsulated in liposomes or biodegradable polymeric microparticles or nanoparticles. In all cases, the ultimate dosage form must be sterile, fluid and stable under the conditions of manufacture and storage. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride, i.e., to use physiological salt (saline) solutions. Prolonged absorption of the injectable compositions can be brought about by the use in the compositions of agents delaying absorption, for example, aluminum monostearate and gelatin.

Sterile injectable or infusable solutions are prepared by incorporating the active compound in the required amount in the appropriate solvent, such as DMSO, or water, including physiological salt solutions, which can comprise agents such as cyclodextrin, to improve dispersion of the lipid soluble steroid in aqueous media, along with various other ingredients enumerated above, as required, followed by sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The principal active ingredient is compounded for convenient and effective administration in effective amounts with a suitable pharmaceutically acceptable carrier in a dosage unit form as hereinbefore disclosed. A unit dosage form, such as a preselected amount of liquid composition, can, for example, contain the principal active compound in amounts ranging from about 5 to about 1000 mg, with from about 250 to about 750 mg being preferred. Expressed in proportions, the active compound is generally present in from about 10 to about 750 mg/ml of carrier. Liquid formulations of progesterone can comprise about 1–100 mg/ml of vehicle. In the case of compositions containing supplementary active ingredients, the dosages are determined by reference to the usual dose and manner of administration of the said ingredients.

As used herein with respect to delivery vehicle, the term "consisting essentially of" is defined to mean that the vehicle, e.g., DMSO, water intravenous salt solutions or aqueous suspensions containing liposomes, cyclodextrins, creamophor or suspending agents, may contain minor amounts, e.g., generally less than 1–5 wt-% of pharmaceutically acceptable solvents and adjuvants, as discussed hereinbelow.

The active ingredients of the therapeutic compositions and the compounds of the present invention can exhibit anti-stroke activity when administered in amounts ranging from about 0.1 mg to about 100 mg per kilogram of body weight per day. A preferred dosage regimen for optimum results would be from about 0.5 mg to about 50 mg per kilogram of body weight per day, and such dosage units are employed that a total of from about 0.25 gram to about 3.0 grams of the active compound for a subject of about 70 kg of body weight are administered in a 24-hour period. This dosage regimen may be adjusted to provide the optimum therapeutic response and is preferably administered one to three times a day in dosages of about 600 mg per administration. For example, several divided doses may be administered daily or the dose may be proportionally reduced as indicated by the exigencies of the therapeutic situation. A decided practical advantage is that the active compound may be administered in a convenient manner such as by the oral, intravenous, intramuscular or subcutaneous routes.

Useful dosages of the progestin, i.e., of progesterone, can be determined from their in vitro activity, and in vivo activity in animal models and, to some extent, from the dosages found to exert other pharmacological effects in humans. Methods for the extrapolation of effective dosages in mice, and other animals, to humans are known to the art; for example, see U.S. Pat. No. 4,938,949.

The invention will be further described by reference to the following detailed examples.

EXAMPLE 1

Evaluation of Progesterone in Stroke Model
1. Materials and Methods

Male Wistar rats (n=48) weighing 270–300 g were employed in all experiments. The effect of exogenously administered PROG on the male and not the female rat was tested in order to exclude complicating effects on ischemic cell damage of hormonal fluctuations during the estrus cycle. Nonfasted animals were anaesthetized with 3.5% halothane, and maintained with 1.0–2.0% halothane in 70% $N_2O$ and 30% $O_2$ using a face mask. Rectal temperature was maintained at 37° C. throughout the surgical procedure using a feedback regulated water heating system. The right femoral artery was cannulated with medical grade silicone tubing (Technical Products, Inc., Decatur, Ga.) for monitoring blood pressure, and for sampling of blood for blood gas measurements (pH, $pO_2$, $pCO_2$) before and 20 minutes after initial administration of PROG or vehicle.

Middle cerebral artery (MCA) occlusion (MCAO) was induced, as previously described by H. Chen et al., *J. Cereb. Blood Flow Metab.*, 12, 621 (1992) and J. Koizumi et al., *Jpn. J. Stroke*, 8, 1 (1986). Briefly, the right common carotid artery, external carotid artery (ECA) and internal carotid artery (ICA) were exposed. A length of 4-0 monofilament nylon suture (18.5–19.5 mm), determined by the animal weight, with its tip rounded by heating near a flame, was advanced from the ECA into the lumen of the ICA until it blocked the origin of the MCA. Two hours after MCAO, animals were reanaesthetized with halothane and reperfusion was performed by withdrawal of the suture until the tip cleared the lumen of the ICA.

Four randomly assigned populations of animals were tested. Group 1 (n=12): water soluble PROG (PROG with balance of 2-hydroxypropyl-β-cyclodextrin) (Sigma Chemical Co., St Louis, Mo.) dissolved in saline (4.0 mg/ml) was injected intraperitoneally (4.0 mg/kg) 30 minutes before MCAO. The remaining injections (all 4.0 mg/kg) were given at 6 and 24 hours after MCAO, respectively. Group 2 (n=12): the experimental protocol was identical to that in Group 1, except that PROG (4-pregnene-3,20-dione) (Sigma Chemical Co., St Louis, Mo.) dissolved in dimethyl sulfoxide (DMSO; Sigma Chemical Co., St Louis, Mo.) (8.0 mg/ml), instead of water soluble PROG, was administered. Group 3 (n=12): the experimental protocol was identical to that in group 2, except that the initial injection was delayed to the onset of reperfusion (2 hours after MCAO). Group 4 (n=12): the experimental protocol was the same as that in Group 2, except that the same volume of DMSO without PROG (0.5 ml/kg) as in Group 2 was administered.

In a preliminary pharmacokinetic study (n=2) using Coat-A-Count PROG Procedure kit (Diagnostic Products Co., Los Angeles, Calif.), a solid-phase radioimmunoassay, demonstrated that PROG was absorbed rapidly by the intraperitoneal route of administration; the plasma level of PROG increased to 41.9 and 70.7 ng/ml 4 hours after administration of DMSO dissolved PROG at the dose of 4.0 mg/kg from the pre-injection level of 7.17 and 5.29 ng/ml, respectively.

All animals were weighed before surgery for MCAO and at 24 and 48 hours after MCAO. Neurological abnormalities were also evaluated 24 and 48 hours after MCAO using the scale (0–4) described by Z. Longa et al., *Stroke*, 20, 84 (1989). Rats were held gently by the tail, suspended one meter above the floor, and observed for forelimb flexion. Normal rats that extend both forelimbs toward the floor and that exhibited no other neurological deficit were assigned grade 0. Rats that consistently flexed the left forelimb (contralateral to the injured hemisphere) accompanying flexion of the wrist toward left without any other abnormality were graded 1. Rats that were allowed to move about freely and circled toward the paretic side consistently were graded 2. Rats that fell down to the left losing the ability to walk were graded 3. Rats that exhibited a depressed level of consciousness were graded 4.

Forty-eight hours post MCAO, the animals were reanaesthetized with ketamine (44 mg/kg) and xylazine (13 mg/kg). Transcardiac perfusion with heparinized saline was performed on all animals to remove blood from cerebral vessels. Thereafter, the animals were decapitated, and the brains were quickly removed. Each brain was cut into 2-mm thick coronal sections (7 sections per brain) using a rat brain matrix and was then stained for 30 minutes in a 2% solution of 2,3,5-triphenyltetrazolium chloride (TTC) at 37° C. TTC, a tetrazolium salt, reacts with mitochondrial respiratory enzymes and is reduced to a red formazan-insoluble product by electron acceptance. This reaction is lost in damaged mitochondria or oxidative systems, and the lack of staining demarcates ischemic from normal brain tissue (J. B. Bederson et al., *Stroke*, 17, 1304 (1986)). After TTC staining, the tissues were fixed by immersion in 10% buffered formalin solution. Each TTC stained section was photographed with a 35-mm camera mounted on an operating microscope within 2 days of TTC staining. The unstained area as well as the total right and left hemispheric area for each coronal section were traced using the Global Lab Image analysis system (Data Translation, Malboro, Mass). The indirect lesion area, in which the intact area of the ipsilateral hemisphere was subtracted from the area of the contralateral hemisphere, was calculated (R. A. Swanson et al.,*J. Cereb. Blood Flow Metab.*, 10, 290 (1990)). Infarct, and left and right hemisphere volumes ($mm^3$) were determined by multiplying the respective corresponding areas by the section interval thickness. The lesion volume is presented as a volume percentage of lesion compared to the contralateral hemisphere.

For parametric variables, a one way ANOVA was applied to determine the statistical significance of differences among groups. If a significant difference was detected, then two sample t-tests with Bonferroni correction were performed to evaluate differences between control and PROG treated groups. Paired t-tests were performed on physiological parameters before and after administration of PROG and DMSO within each group. Values presented in this study are mean ±S.E.M. A probability value less than 0.05 was considered significant.

2. Results

The physiological variables before and after initial PROG/DMSO treatments are shown in Table 1. All values were within the normal range for rats and there was no significant difference in physiological variables before and after injection of either PROG or DMSO.

TABLE 1

Physiological parameters (n = 12/group)

| Group | PROG in saline | PROG pre-MCAO | PROG post-MCAO | DMSO |
|---|---|---|---|---|
| Pre-injection | | | | |
| pH | 7.44 ± 0.01 | 7.44 ± 0.01 | 7.46 ± 0 | 7.46 ± 0 |
| $pCO_2$ (mm Hg) | 41 ± 1 | 41 ± 1 | 36 ± 1 | 39 ± 1 |
| $pO_2$ (mm Hg) | 122 ± 5 | 134 ± 4 | 133 ± 4 | 135 ± 3 |
| Mean Blood Pressure (mm Hg) | 94 ± 3 | 94 ± 3 | 107 ± 3 | 102 ± 2 |
| 20 min post-injection | | | | |
| pH | 7.42 ± 0.02 | 7.43 ± 0.02 | 7.44 ± 0.01 | 7.40 ± 0.01 |
| $pCO_2$ (mm Hg) | 41 ± 1 | 39 ± 2 | 36 ± 1 | 43 ± 1 |

TABLE 1-continued

Physiological parameters (n = 12/group)

| Group | PROG in saline | PROG pre-MCAO | PROG post-MCAO | DMSO |
|---|---|---|---|---|
| $pO_2$ (mm Hg) | 123 ± 14 | 135 ± 5 | 134 ± 3 | 131 ± 4 |
| Mean Blood Pressure (mm Hg) | 94 ± 3 | 95 ± 2 | 103 ± 3 | 102 ± 3 |

Values are mean ± S.E.M.

As shown in Table 2, the percent infarct volume was significantly decreased in both DMSO dissolved PROG pre-treated (39%, t=2.5616, P=0.018) and delayed treated (34%, t=2.3690, P=0.027) groups compared with the DMSO treated control group. The difference of infarct in water soluble PROG treated group in relation to the DMSO treated control group is not statistically significant (18%, t=1.0833, P=0.290). FIG. 1 shows the distribution of percent area of infarct in each of the seven brain sections from all the four groups.

TABLE 2

The percent infarct volume to the contralateral hemisphere in the 4 experimental groups (n = 12/group)

| Group | PROG in saline | PROG pre-MCAO | PROG post-MCAO | DMSO |
|---|---|---|---|---|
| % Infarct volume | 28.7 ± 3.8 | 21.5 ± 2.9* | 23.1 ± 2.3* | 35.1 ± 4.5 |

Values are mean ± S.E.M.
*P < 0.05 versus DMSO group.

Table 3 presents results of body weight loss and the neurological deficit score 24 and 48 hours after onset of ischemia in each group. Both groups of regular PROG treated animals exhibited a significantly improved physiological response as reflected by a reduced body weight loss and improved neurological function (lower score) compared with the DMSO group.

TABLE 3

Body weight loss (grams) and the neurological deficit (score) daily after MCAO (n = 12/group)

| Group | PROG in saline | PROG pre-MCAO | PROG post-MCAO | DMSO |
|---|---|---|---|---|
| Weight Loss | | | | |
| 24 h | 36.5 ± 3.3 | 31.1 ± 2.6* | 33.8 ± 1.9 | 40.4 ± 3.4 |
| 48 h | 13.3 ± 3.1 | 8.8 ± 2.2** | 10.0 ± 3.1* | 19.7 ± 2.9 |
| Neurologic Score | | | | |
| 24 h | 1.7 ± 0.1 | 1.4 ± 0.1* | 1.4 ± 0.1* | 1.8 ± 0.1 |
| 48 h | 1.7 ± 0.1 | 1.4 + 0.1* | 1.4 ± 0.1* | 1.8 ± 0.1 |

Values are mean ± S.E.M.
*P < 0.05.
**P < 0.01 versus DMSO group.

EXAMPLE 2

I. V. Administration of Progesterone in Saline Post-MCAO

Following the methodology of Example 1, three randomly assigned populations of animals were tested. Group 1 (n=7, saline controls); Group 2 (n=7, water-soluble PROG dissolved in saline 4.0 mg/ml was injected intravenously (4.0 mg/kg) two hours after induction of MCAO); Group 3 (n=7, PROG injected i.v. (8 mg/kg) two hours after induction of MCAO).

Functional and neurological outcome measures were performed for all experimental groups. These measures included: the accelerating rotarod test, somatosensory tab removal, weight loss and gross neurological examination using the Zea Longa test described in Example 1.

The accelerating rotarod measures the time a rat remains on a rotating treadmill. This is an index of motor function and balance. The rats are trained prior to ischemia to remain on the treadmill and the time on the rotarod is measured for each rat. Daily after stroke, the rat is placed on the treadmill and time before fall is measured.

The somatosensory measurement involves placement of a round colored paper tab on the forelimb of the rat. Prior to ischemia, the rat senses the presence of the tab and removes it within seconds, after ischemia the time of removal is delayed. Measurement of the time for removal of the tab provides a sensitive index of somatosensory function.

Weight loss provides an index of general physiological status. Animals with large weight loss have worse strokes and persistent weight loss is an indication of poor recuperation.

The gross neurological examination measures limb weakness and circling as an index of stroke deficit as described in Example 1. The rotarod and somatosensory tests are considered the most sensitive tests for neurologic recovery.

The main analysis approach measures analysis of variance for the variables which were collected daily for seven days. This analysis gave test results for a time effect, for a treatment group effect and for time by treatment interaction. For lesion size, one way analysis of variance was used for the main testing. Correlations between each outcome and lesion volume were computed within each treatment group.

Figure 2:
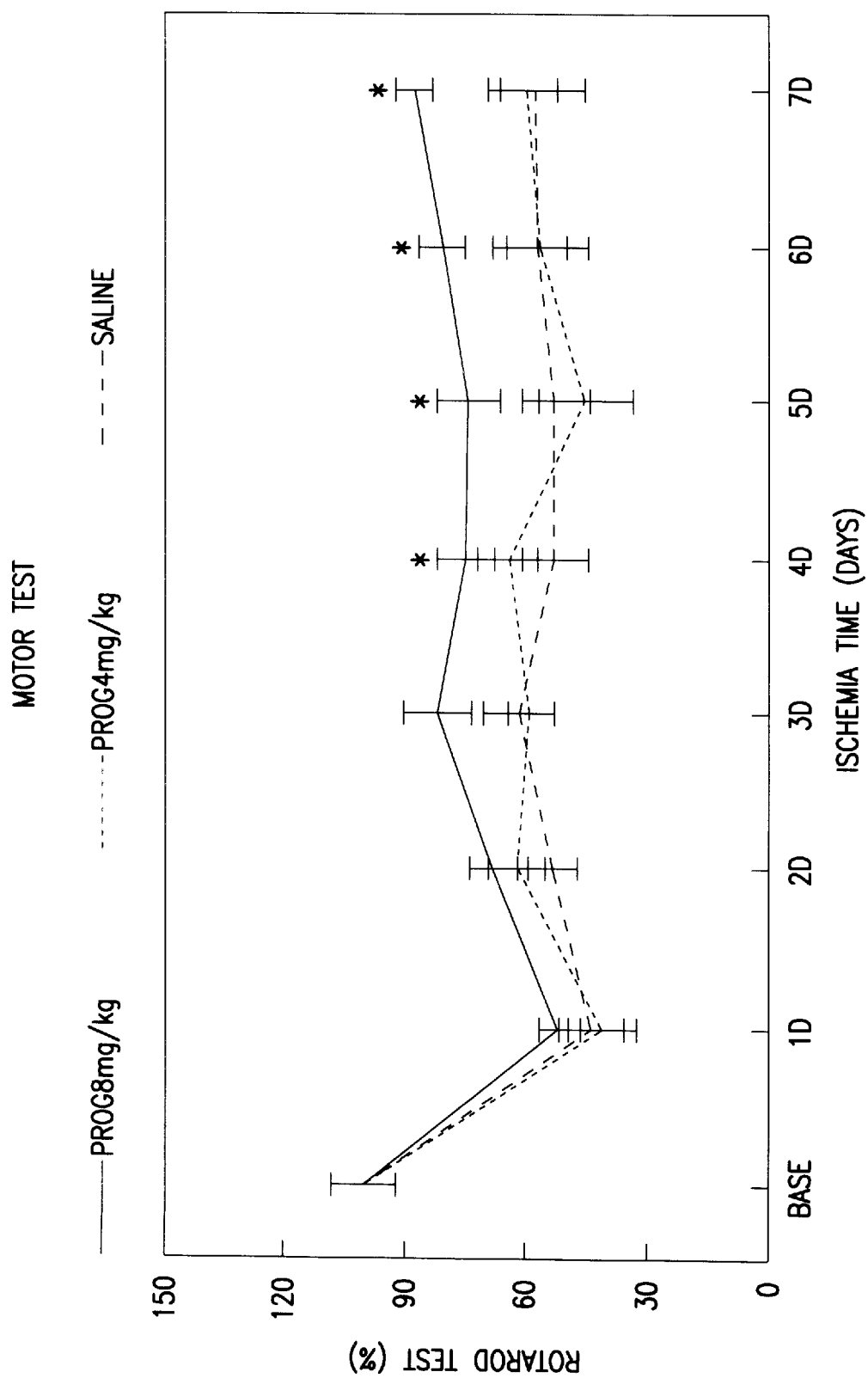
FIG. 2 is a graph summarizing the results of a motor function test in the rat model of MCAO (—=PROG 8 mg/kg;—=PROG 4 mg/kg;—•—=saline; d=days (Values are mean ±S.E.M. P<0.05 versus saline)).
Figure 3:
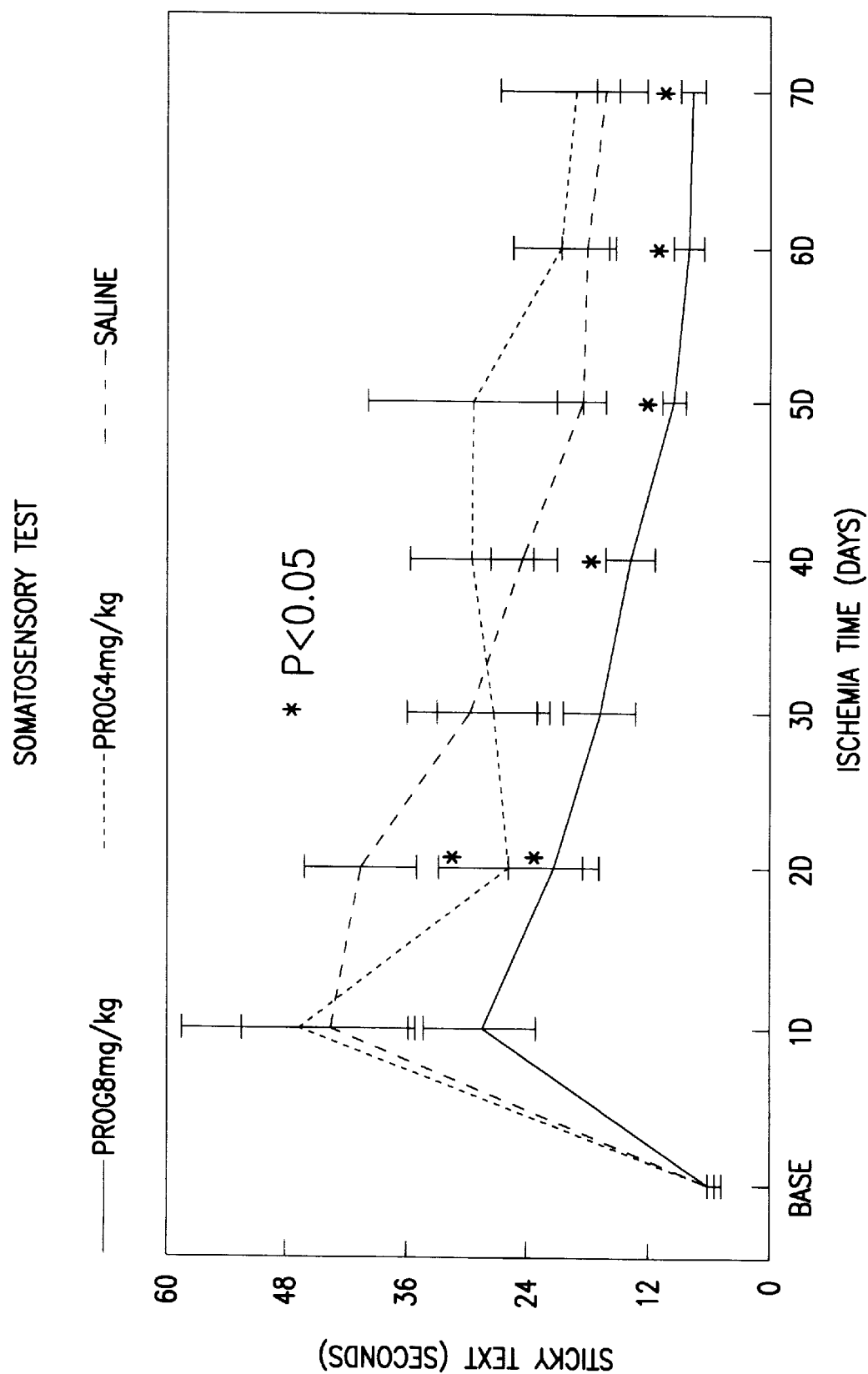
FIG. 3 is a graph depicting the results of the somatosensory test (tab removal from forelimb="sticky test") in the rat model of MCAO (symbols as in FIG. 2).
Figure 4:
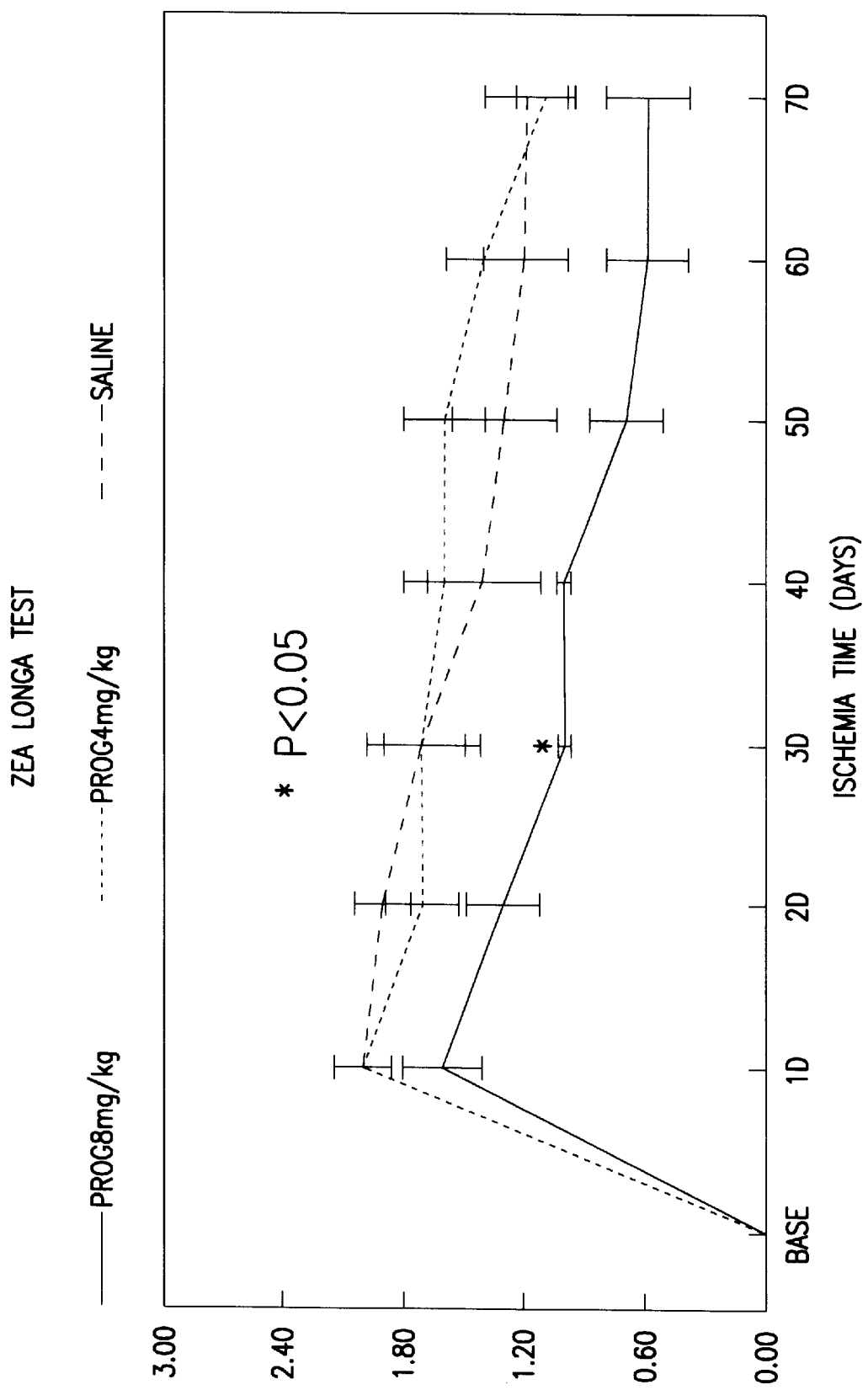
FIG. 4 is a graph depicting the results of neurological examination by the Zea Longa test in the rat model of MCAO (symbols as in FIG. 2).
Figure 5:
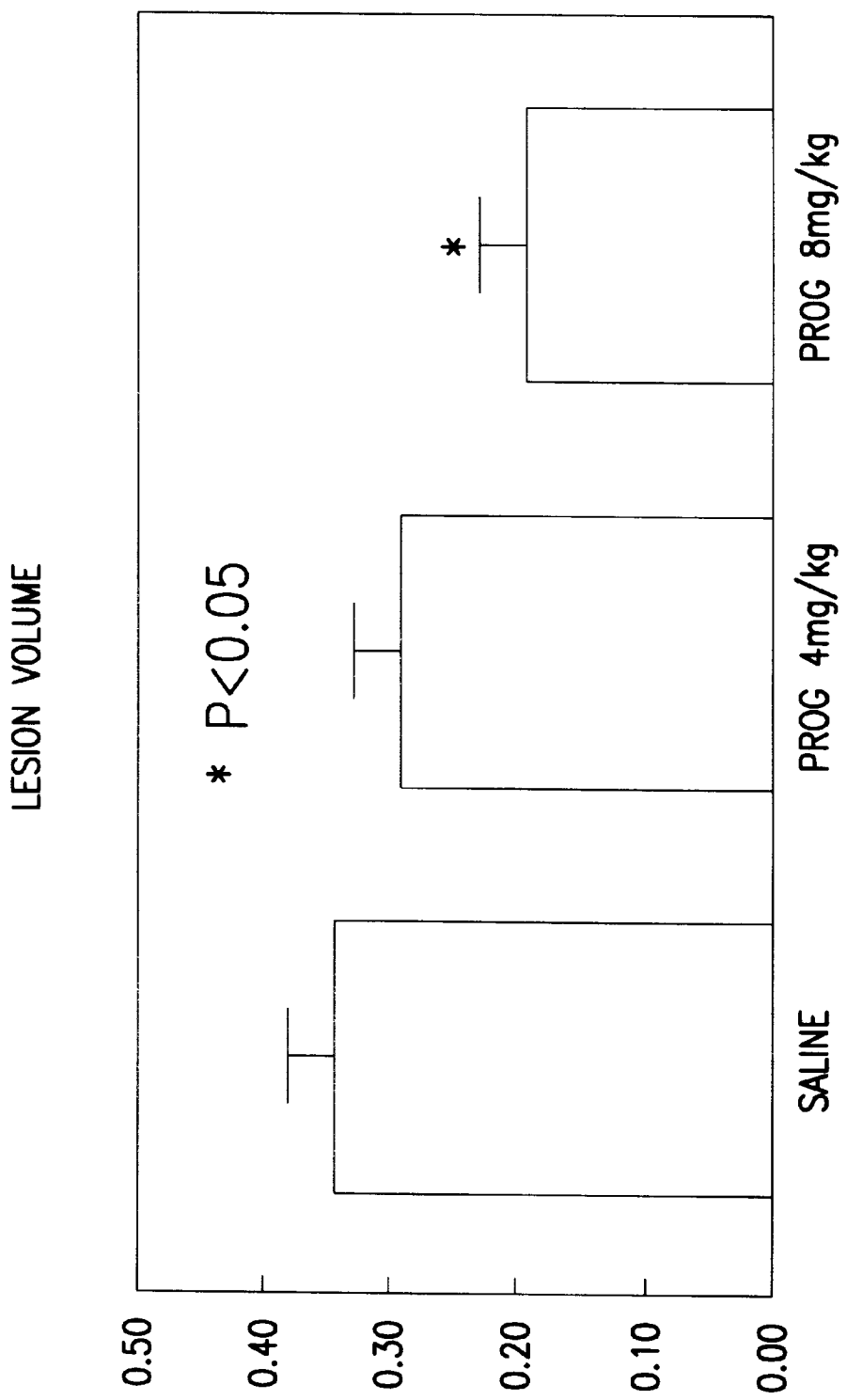
FIG. 5 is a bar graph depicting lesion volume in the rat MCAO model.

Plots of the repeated outcomes are given in FIGS. 2–4, attached. Lesion volume results, measured as described in Example 1, are summarized in FIG. 5. Except for weight (data not shown), all of the outcomes show a treatment effect.

As shown in FIGS. 2–5, the data demonstrated that treatment of the rat with 8 mg/kg of progesterone in saline post MCAO, significantly improved neurologic outcome compared with non-treated or treated animals treated with 4 mg/kg of progesterone. The temporal profile of rotarod, somatosensory and gross neurologic function was significantly altered and improved in the 8 mg/kg group and lesion volume was reduced. There was no benefit from the 4 mg/kg dose. These data indicate that progesterone significantly reduces neurological deficits after stroke and is a highly efficacious treatment for stroke in this animal model.

Although the mechanisms underlying the neuroprotection against cerebral ischemia by PROG are unknown, influencing brain excitability may be one of them. Potentiating the GABA receptor and/or inhibiting EAA receptors, especially N-methyl-D-aspartate (NMDA) subtype of the glutamate receptor, can offer protection against ischemic damage. In vivo studies have established that physiological levels of PROG enhance GABA-mediated inhibition of neuronal activity (S. S. Smith et al., *Prog. Neurobiol.*, 44, 55 (1994)). PROG rapidly alters the excitability of neurons, in part by potentiating GABA-evoked Cl currents and like other GABA potentiating drugs, PROG possesses anticonvulsant activity (T. G. Kokate et al., *J. Pharmacol. Exp. Ther.*, 270, 1223 (1994)).

Circulating PROG is a lipophilic compound and easily passes through the blood-brain barrier (BBB) and enters the CNS at widespread sites. Once sequestered within the neuronal population, PROG is then metabolized to other more active forms, such as $3\alpha$, $5\alpha$-THP and the levels of the $3\alpha$-hydroxy C21 steroids in CNS parallel cyclic fluctuations of PROG in the circulation.

In conclusion, these examples demonstrate that administration of PROG in DMSO or saline to the male rat before or after transient MCAO reduces ischemic cell damage and improves physiological and neurological function 2–7 days after stroke.

All patents, patent documents and publications cited hereinabove are incorporated by reference herein.

While the invention has been described with reference to certain preferred embodiments, those skilled in the art will realize that changes and modifications may be made thereto without departing from the full and intended scope of the appended claims.

What is claimed is:

1. A therapeutic method comprising treating a mammal afflicted with cell damage due to ischemia, by administering an amount of a progestin to said mammal effective to reduce ischemic injury, wherein said progestin is administered after onset of ischemia.

2. The method of claim 1 wherein the cells damaged due to ischemia are in the central nervous system.

3. The method of claim 2 wherein the mammal has suffered a stroke.

4. The method of claim 3 wherein the mammal is a human.

5. The method of claim 1 wherein the cells damaged due to ischemia are muscle cells.

6. The method of claim 1, 2 or 3 wherein the progestin is administered parenterally.

7. The method of claim 6 wherein the progestin is administered intravenously.

8. The method of claim 7 wherein the progestin is administered by injection or infusion.

9. The method of claim 1 wherein the progestin is administered to a human in combination with a pharmaceutically acceptable vehicle.

10. The method of claim 9 wherein the vehicle is dimethyl sulfoxide.

11. The method of claim 9 wherein the vehicle is water or a physiological saline solution.

12. The method of claim 1 or 9 wherein the progestin is progesterone.

13. The method of claim 1 or 9 wherein the progestin is allopregnanolone.

14. The method of claim 1 or 9 wherein the progestin is 5-dehydroprogesterone.

15. The method of claim 1 or 9 wherein the progestin is 5-pregnane-3,20-dione.

16. A pharmaceutical composition consisting essentially of an amount of a progestin effective to treat ischemic cell damage dissolved or dispersed in dimethyl sulfoxide.

17. The pharmaceutical composition of claim 16 wherein the progestin is progesterone.

18. The pharmaceutical composition of claim 16 wherein the progestin is allopregnanolone.

19. The pharmaceutical composition of claim 16 wherein the progestin is 5-dehydroprogesterone.

20. The pharmaceutical composition of claim 16 wherein the progestin is 5-pregnane-3,20-dione.

* * * * *